US009818309B2

(12) United States Patent
Snyder

(10) Patent No.: US 9,818,309 B2
(45) Date of Patent: *Nov. 14, 2017

(54) HYDRATION LEVEL MEASUREMENT SYSTEM AND METHOD

(71) Applicant: HUMANA INC., Louisville, KY (US)

(72) Inventor: Seth Snyder, Providence, RI (US)

(73) Assignee: HUMANA INC., Louisville, KY (US)

( * ) Notice: Subject to any disclaimer, the term of this patent is extended or adjusted under 35 U.S.C. 154(b) by 359 days.

This patent is subject to a terminal disclaimer.

(21) Appl. No.: 14/660,536

(22) Filed: Mar. 17, 2015

(65) Prior Publication Data

US 2016/0358507 A1 Dec. 8, 2016

Related U.S. Application Data

(63) Continuation of application No. 13/004,578, filed on Jan. 11, 2011, now Pat. No. 8,979,539.

(60) Provisional application No. 61/293,833, filed on Jan. 11, 2010.

(51) Int. Cl.
*G09B 19/00* (2006.01)
*G06F 19/00* (2011.01)
*G01G 21/00* (2006.01)
*G09B 5/10* (2006.01)

(52) U.S. Cl.
CPC ......... *G09B 19/0092* (2013.01); *G01G 21/00* (2013.01); *G06F 19/3475* (2013.01); *G09B 5/10* (2013.01)

(58) Field of Classification Search
CPC .. G09F 19/3475; G09B 19/0092; G09B 19/00
USPC ........................................ 434/127, 236, 238
See application file for complete search history.

(56) References Cited

U.S. PATENT DOCUMENTS

| | | | | |
|---|---|---|---|---|
| 6,252,494 | B1 * | 6/2001 | Howell | A47G 23/16 340/309.3 |
| 7,801,642 | B2 * | 9/2010 | Ansari | G06F 19/327 700/215 |
| 8,201,736 | B2 * | 6/2012 | Doglioni Majer | G07F 9/02 194/216 |
| 8,202,217 | B2 * | 6/2012 | Howell | A61B 5/01 221/15 |

(Continued)

*Primary Examiner* — Sam Yao
*Assistant Examiner* — Michael Humphrey
(74) *Attorney, Agent, or Firm* — Standley Law Group LLP

(57) ABSTRACT

A hydration level measurement system and method comprising a technology embedded scale that rewards individuals for drinking an appropriate amount of liquid throughout the day. In an example embodiment, a reusable water bottle is equipped with an RFID tag and assigned to an individual so that the user's hydration level may be tracked. The RFID tag logs the individual's access as well as "before-filling" and "after-filling" weights of the bottle when placed on the scale. A computer screen acknowledges the bottle's owner, and then indicates the increased weight and how many points will be awarded to the user using an ounces-to-points conversion. Data may be transferred from the scale computer to a web server and aggregated at the server from multiple scales for multiple "hydration challenges." A web application receives and processes user requests to display data related to each hydration challenge such as the current scores of the participants.

17 Claims, 8 Drawing Sheets

(56) References Cited

U.S. PATENT DOCUMENTS

| | | | |
|---|---|---|---|
| 8,267,694 B1* | 9/2012 | Lamka | G09B 19/0038 434/236 |
| 8,884,752 B2* | 11/2014 | Tai | G06Q 50/24 340/539.1 |
| 2004/0102931 A1* | 5/2004 | Ellis | A61B 5/1038 702/188 |
| 2004/0131997 A1* | 7/2004 | McGuire | G09B 19/0092 434/127 |
| 2004/0247748 A1* | 12/2004 | Bronkema | G06F 19/3481 426/106 |
| 2005/0287502 A1* | 12/2005 | Southard | G09B 19/0092 434/236 |
| 2006/0036395 A1* | 2/2006 | Shaya | G01G 19/4146 702/127 |
| 2006/0041330 A1* | 2/2006 | Ansari | G06Q 10/087 700/240 |
| 2006/0131404 A1* | 6/2006 | Dervishian | G06Q 99/00 235/385 |
| 2006/0231109 A1* | 10/2006 | Howell | A61B 5/6887 128/898 |
| 2006/0238346 A1* | 10/2006 | Teller | B67D 3/0077 340/572.1 |
| 2006/0241355 A1* | 10/2006 | Howell | A61B 5/01 600/300 |
| 2006/0294033 A1* | 12/2006 | Quraishi | G09B 19/0092 705/500 |
| 2007/0048224 A1* | 3/2007 | Howell | A61B 5/4277 424/9.1 |
| 2008/0064016 A1* | 3/2008 | Aruffo | G09B 19/0092 434/262 |
| 2008/0077489 A1* | 3/2008 | Gilley | G06Q 30/02 705/14.11 |
| 2008/0077619 A1* | 3/2008 | Gilley | G06Q 30/02 |
| 2008/0082360 A1* | 4/2008 | Bailey | G06Q 10/06 705/2 |
| 2008/0197969 A1* | 8/2008 | Vogt | G06Q 10/087 340/5.8 |
| 2008/0228523 A1* | 9/2008 | Derienz | G01G 19/4146 705/2 |
| 2008/0234600 A1* | 9/2008 | Marsh | A61B 5/01 600/549 |
| 2008/0267444 A1* | 10/2008 | Simons-Nikolova | A61B 5/1123 382/100 |
| 2008/0280278 A1* | 11/2008 | Chu | G09B 19/0092 434/238 |
| 2009/0127339 A1* | 5/2009 | Needhan | G06F 19/3456 235/454 |
| 2009/0276161 A1* | 11/2009 | Cobain | G06F 19/3431 702/19 |
| 2010/0003653 A1* | 1/2010 | Brown | G09B 19/0092 434/236 |
| 2010/0111383 A1* | 5/2010 | Boushey | G06K 9/00 382/128 |
| 2010/0125178 A1* | 5/2010 | Hyde | G09B 19/0092 600/300 |
| 2010/0283601 A1* | 11/2010 | Tai | G06Q 50/24 340/539.12 |
| 2011/0029262 A1* | 2/2011 | Barkhouse | G01F 23/00 702/55 |
| 2011/0121032 A1* | 5/2011 | Deo | B67D 1/0027 222/145.1 |
| 2011/0318717 A1* | 12/2011 | Adamowicz | G09B 19/0092 434/127 |
| 2012/0097566 A1* | 4/2012 | Steadman | B65D 25/56 206/459.1 |
| 2012/0135384 A1* | 5/2012 | Nakao | A23L 33/30 434/127 |

* cited by examiner

HYDRATION LEVEL MEASUREMENT SYSTEM AND METHOD

CROSS-REFERENCE TO RELATED APPLICATION

This application claims priority to U.S. patent application Ser. No. 13/004,578, filed Jan. 11, 2011, titled Hydration Level Measurement System and Method and to U.S. Provisional Patent Application Ser. No. 61/293,833, filed Jan. 11, 2010, titled Hydration Level Measurement System and Method, the contents of each of which are incorporated herein by reference.

BACKGROUND

Water is the most abundant component of the body it is used in nearly all bio-chemical reactions so it is essential that an individual replace the water that is used by the body for such activities as regulation of body temperature as well as other bodily processes that contribute to a healthy life. Maintaining a proper level of hydration is essential to healthy living. Although proper hydration is important for maintaining healthy living, many individuals do not know how much water they consume or whether they are consuming an appropriate level of liquids. Therefore, there is a need for a system and method for easily determining an individual's level of liquid consumption and motivating an individual to maintain an appropriate level of liquid consumption. There is a need for a system and method that allows individuals to track how much water they are consuming while creating goals to motivate them to stay hydrated throughout the day.

SUMMARY

The present disclosure describes a technology embedded scale that rewards individuals for drinking an appropriate amount of water or other liquid throughout the day. In an example embodiment, a reusable water bottle or other drinking vessel is equipped with an RFID tag. The bottle is assigned to an individual so that the user's hydration level may be tracked using the RFID tag. The RFID tag logs the individual's access as well as "before-filling" and "after-filling" weights of the bottle when they place it on the scale. The user's name and the bottle weight information appear on a display at the scale.

The system and method supports users placing an RFID-tagged reusable bottle onto the scale and filling it with a liquid from a pitcher, a water jug, or any other type of liquid container. The scale is connected to a computer that registers each user interaction with the scale. As a user fills a bottle, a computer screen acknowledges the bottle's owner, and then indicates the increased weight and how many points will be awarded the user using a simple ounces-to-points conversion. Data may be transferred from the scale computer to a web server. Data may be aggregated at the server from multiple scales. A web site application receives and processes user requests to display data related to the hydration challenge such as the current scores of the participants.

DETAILED DESCRIPTION

Figure 1:
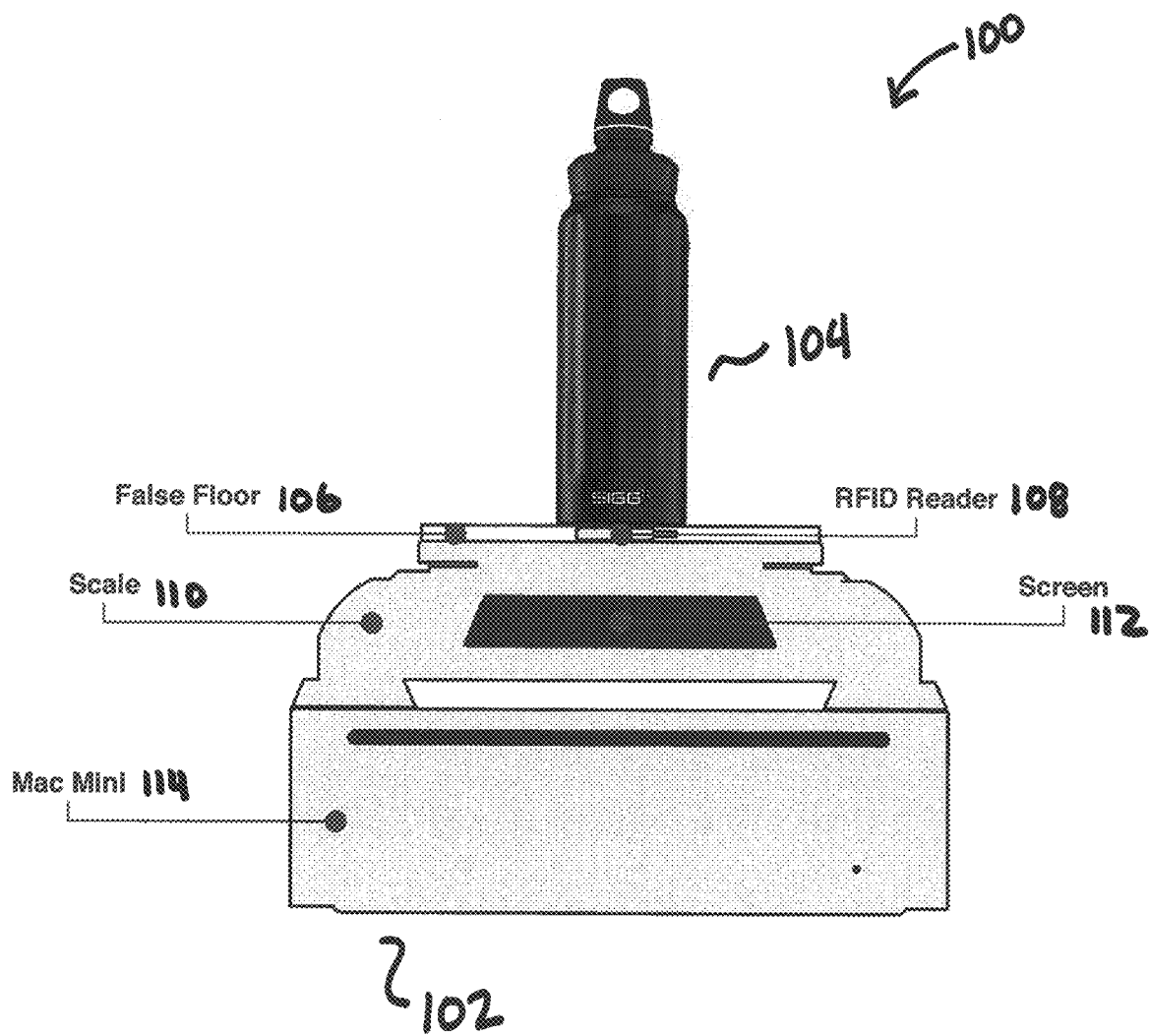
FIG. 1 is a component diagram of a bottle-weighing scale system according to an example embodiment.

Referring to FIG. 1, a component diagram of a bottle-weighing scale system according to an example embodiment is shown. In an example embodiment, the bottle-weighing scale system 100 comprises a bottle 104 or other type of drinking vessel with an attached or embedded RFID tag or other type of electronic identifier. The system base 102 comprises a scale 110 for weighing the bottle 104 and a computer 114 for receiving weight and other data from the scale and transferring it to a web server. The scale 110 is equipped with a false floor 106 that houses an RFID reader 108 or other type of device for detecting an electronic identifier. The scale 110 further comprises a screen 112 for displaying data related to a user's interaction with the scale. In an example embodiment, the computer 114 is an Apple® Mac Mini.

Figure 2:
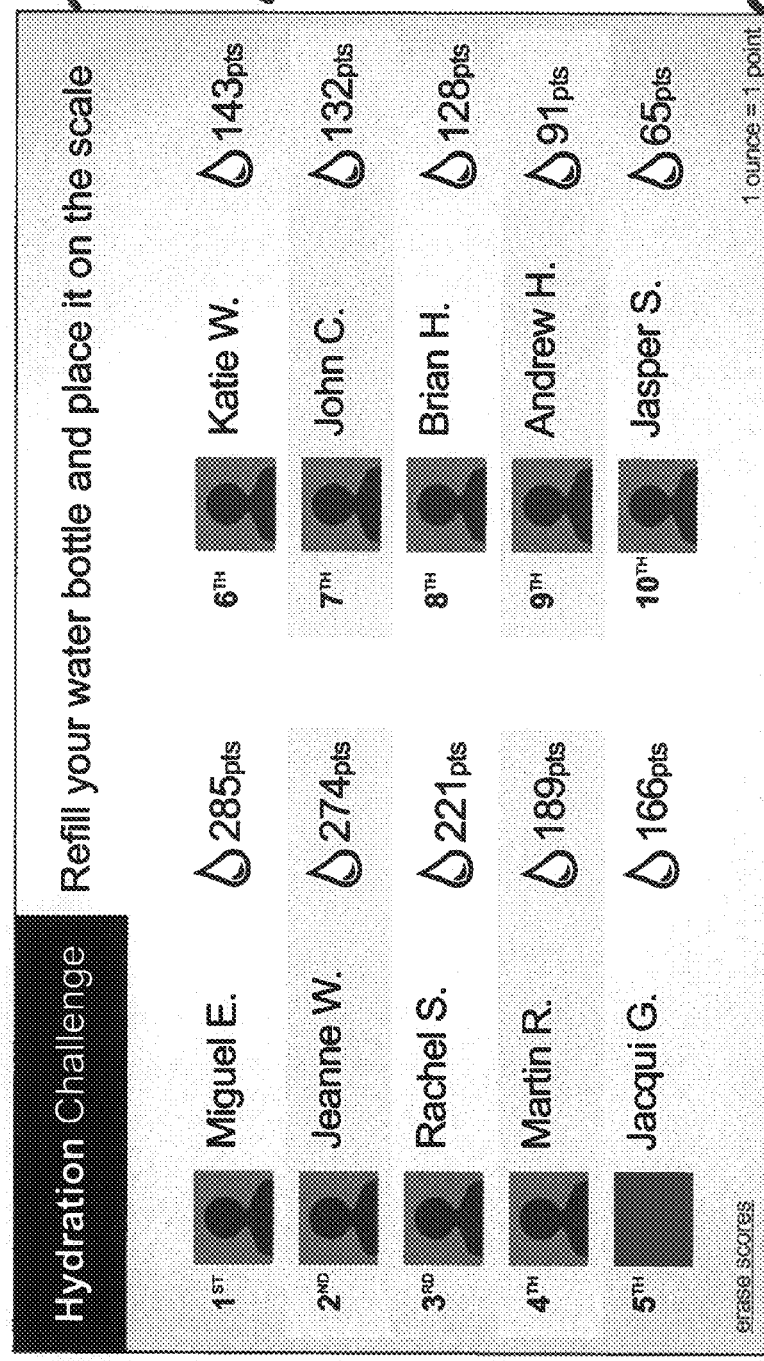
FIGS. 2-8 are sample screens for a computer application according to an example embodiment.

In an example embodiment, the user experience is as follows. Initially, the user places an empty bottle on the scale 110 of the system base 102. The RFID reader 108 scans the tag on the underside of the bottle. The computer screen 112 displays a "welcome user" message to acknowledge a successful scan. Referring to FIG. 2, a sample "fill bottle" screen according to an example embodiment is shown. In a top portion of the computer screen, a message is displayed to instruct the user to fill the bottle and place it on the scale 200. The screen may further display the names and point totals of other participants in the "hydration challenge" 202. Finally, a point conversion indicator 204 may be displayed at the bottom of the screen.

Figure 3:
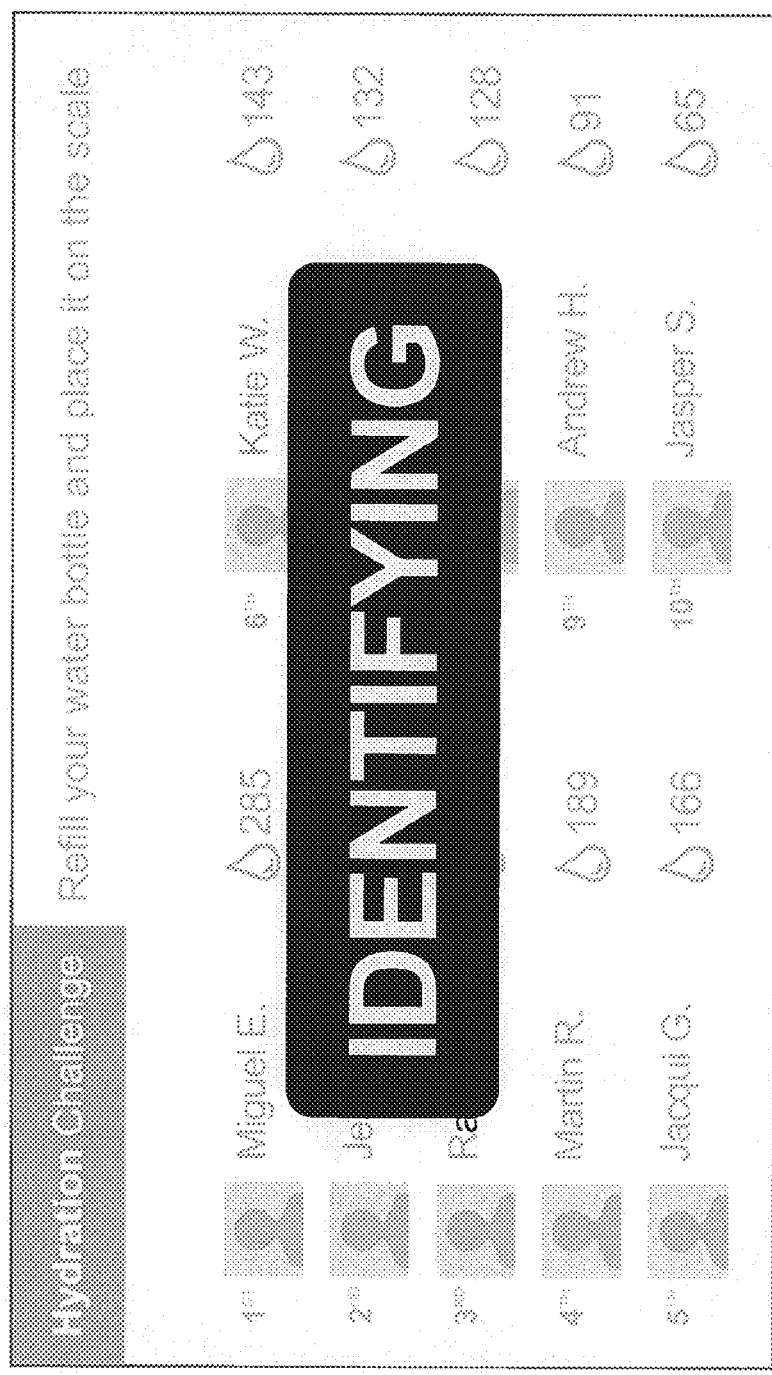

Referring to FIG. 3, a sample "identifying" screen according to an example embodiment is shown. While the RFID read scans the tag on the underside of the bottle and determines the identity of the user, an "identifying" message is displayed to the user to indicate that the computer is performing an operation.

Figure 4:
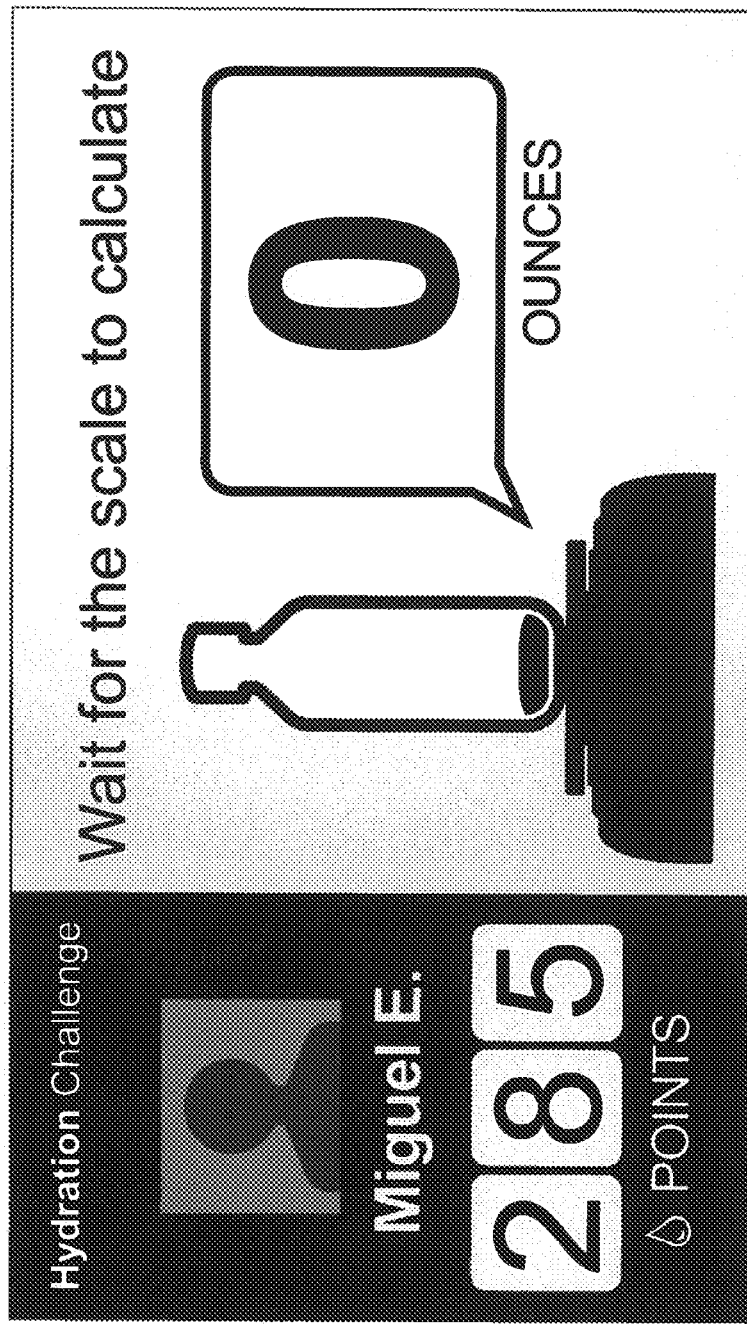

Referring to FIG. 4, a sample "wait" screen according to an example embodiment is shown. A successful scan of the RFID tag is acknowledged by displaying on the screen the user's name and other identifying information (e.g., picture) and the user's current point total 300. A wait message 302 (e.g., "wait for scale to calculate") may be displayed to the user to indicate that the computer is performing an operation.

Figure 5:
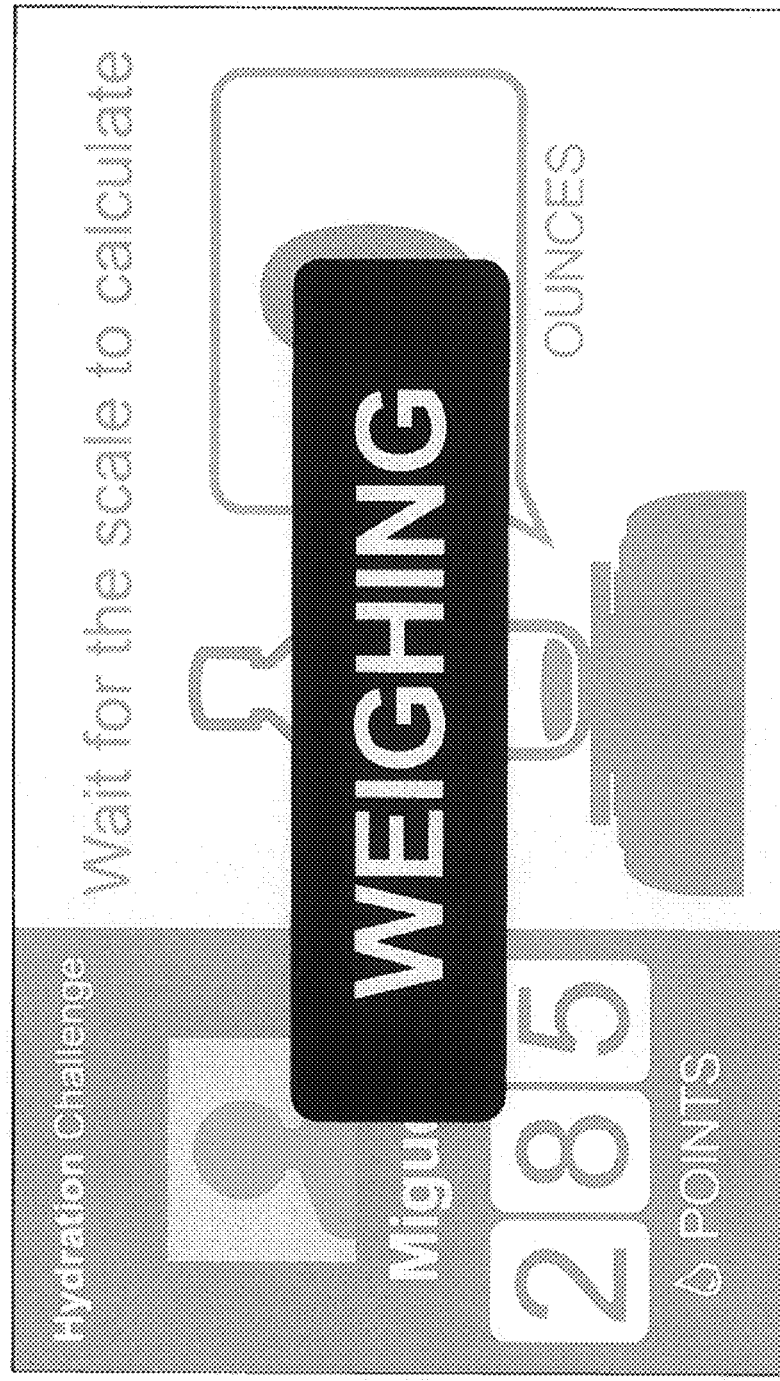

Referring to FIG. 5, a sample "weighing" screen according to an example embodiment is shown. The message indicates to the user that the computer is performing an operation.

Figure 6:

Referring to FIG. 6, a sample "remove" screen according to an example embodiment is shown. After the scale completes the weighing operation, the final weight is displayed 400 and the user is instructed to remove the bottle from the scale. In an example embodiment, the weight is displayed in ounces. Other measurements such as cups, milligrams, grams, etc. may be used.

Figure 7:
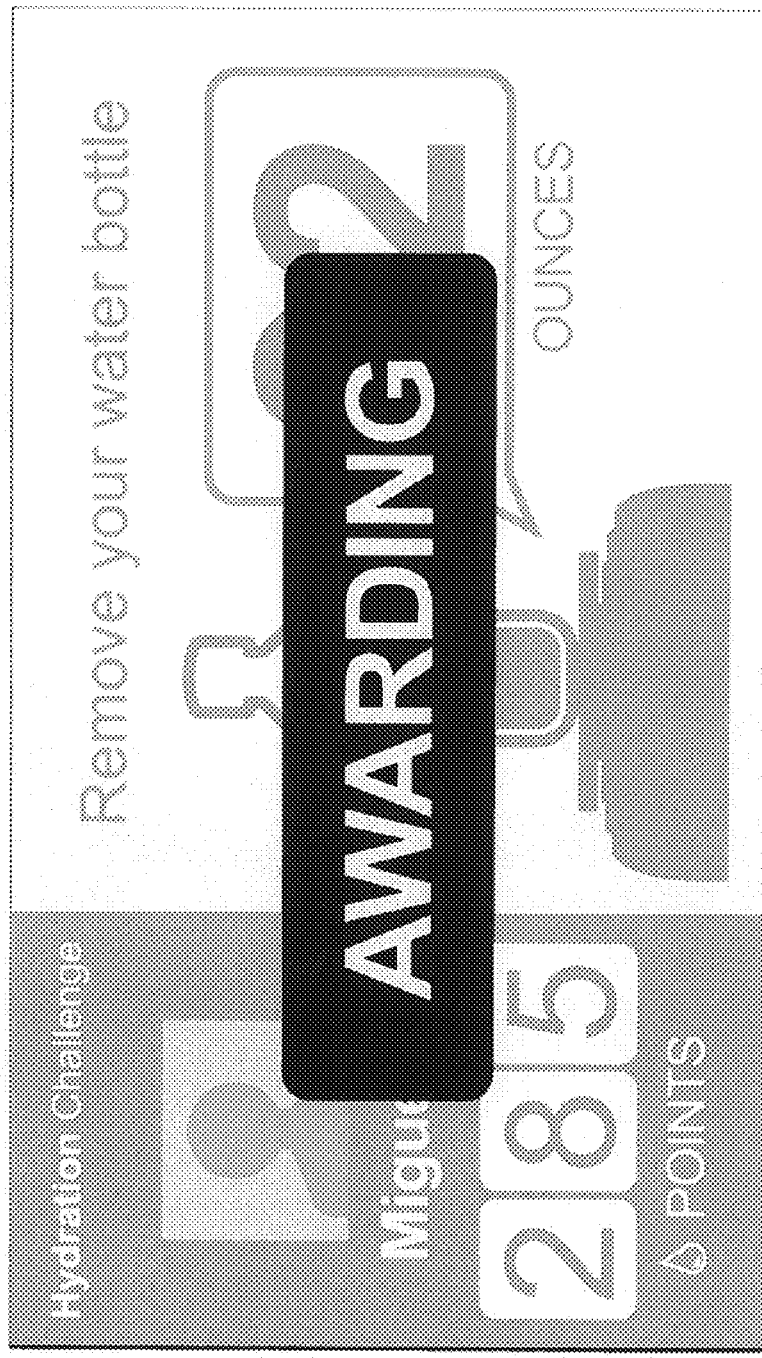

Referring to FIG. 7, a sample "award" screen according to an example embodiment is shown. When the user removes the bottle from the scale, the computer proceeds to add points to the user's point total. The message indicates to the user that the computer is performing an operation.

Figure 8:
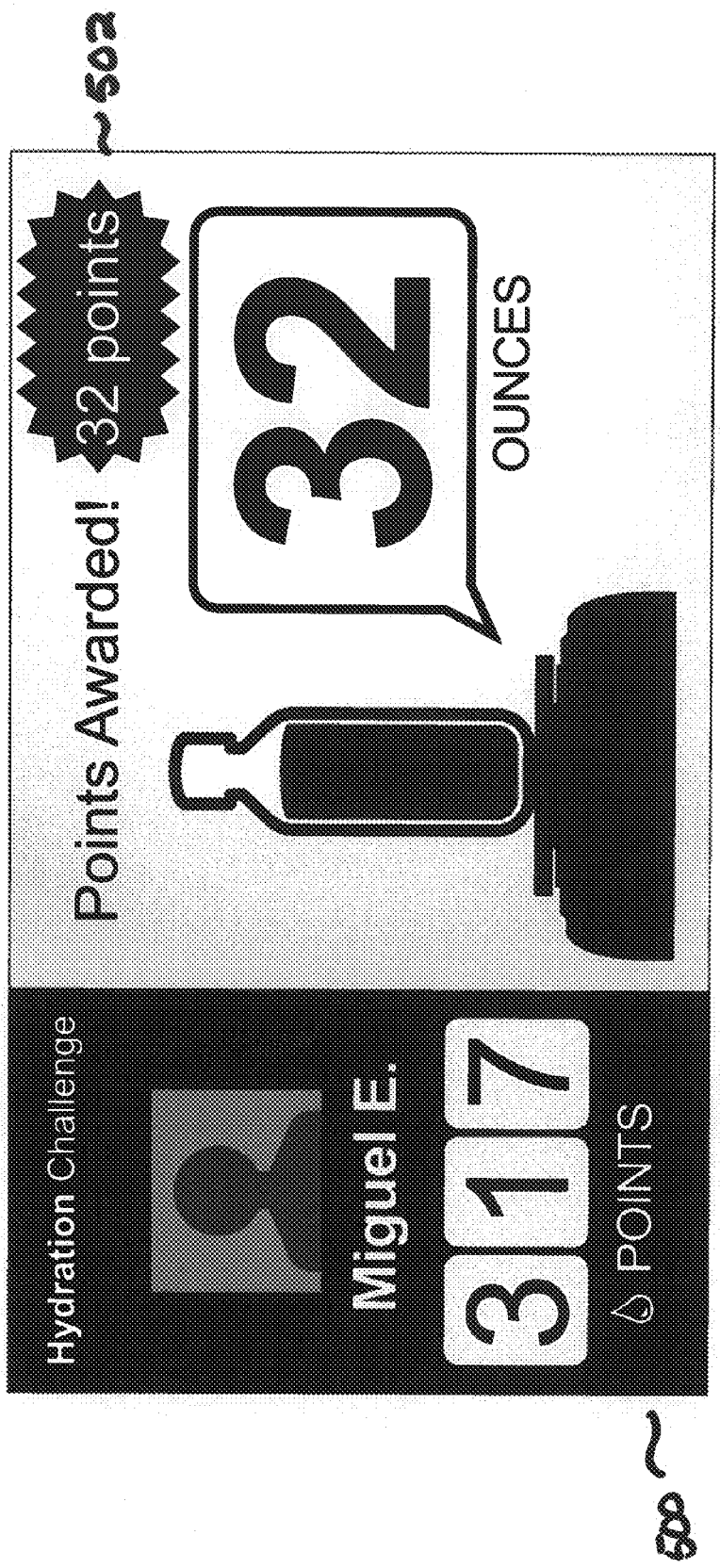

Referring to FIG. 8, a sample "points awarded" screen according to an example embodiment is shown. In an example embodiment, one point is awarded for each ounce of liquid determined to be in the bottle 502. The point is added to the user's total and the user's new point total is also displayed 500. In an example embodiment, the screen is displayed for a set amount of time or until another user scans a bottle at the scale system. If the specified amount of time expires before another user scans a bottle, a welcome screen or other type of screen may be displayed.

User data collected at the scale may be transmitted from the computer to a web server using an Internet connection. Participants may access a browser-based application at the web server to see how others are performing in the "hydration challenge." A plurality of scales may be installed at one or more locations or facilities to increase the number of participants in a single challenge. Each "challenge" may be assigned an identifier that is used to track the individual participants in the challenge. Identifiers for individuals may be assigned to a challenge identifier to create a group of participants for a challenge. Each challenge may also have a start and end date to establish a time period for the challenge. During the challenge time period, the web application may report aggregated user totals across numerous locations or facilities. The user with the greatest number of points on the challenge end date may be declared the "hydration challenge" winner. The reporting of aggregated data and the declaration of a winner may help to increase the level of competition among the participants and cause them to more closely monitor their intake of liquids.

In other embodiments of a hydration level measurement system, a device that detects liquid volume rather than weight may be used. Such a device may use imaging techniques to detect volume changes in a bottle or other drinking vessel. Once a measurement is obtained, the measurement may be converted to points as explained above and the user's point total may be increased in relation to the liquid measurement. Any measurement device that is capable of measuring the liquid in a liquid containing vessel may be used. In addition, any liquid containing vessels capable of having an attached or associated identifier may be used.

A computerized hydration challenge system and method is described in reference to the appended figures. The description with reference to figures is made to exemplify the disclosed computerized system and method and is not intended to limit the system and method to the representations in the figures. From the foregoing description, it can be understood that there are various ways to construct a scale for measuring hydration and awarding points related to hydration levels while still falling within the scope of the present invention. In addition, various types of bottles or drinking vessels as well as attached or associated electronic identifiers may be used and fall within the scope of the present invention. As such, while certain embodiments of the present invention are described in detail above, the scope of the invention is not to be considered limited by such disclosure, and modifications are possible without departing from the spirit of the invention as evidenced by the following claims:

What is claimed is:

1. A hydration level measurement system comprising:
   (a) a liquid containing vessel comprising a vessel identifier;
   (b) a measuring device comprising a vessel identifier detecting device and a scale;
   (c) a computer connected to said measuring device that:
      (1) receives a plurality of user identifiers associated with a challenge, wherein said challenge has start date and an end date, and wherein each user identifier is associated with a challenge total point value that is created at the start date;
      (2) receives from said measuring device the vessel identifier and a first weight reading associated with the liquid containing vessel;
      (3) receives from said measuring device a second weight reading associated with the liquid containing vessel;
      (4) calculates a point value based on a difference between the first weight reading and the second weight reading
      (5) locates the user identifier associated with said vessel identifier;
      (6) calculating a new total point value by adding said point value to the stored challenge total point value associated with said user identifier;
      (7) stores at said computer said new total point value as the stored challenge total point value for said user identifier;
   (d) a display in electronic communication with said computer that displays:
      (1) said user identifiers associated with said challenge; and
      (2) the stored challenge total point value for each user identifier associated with said challenge; and
      (3) said user identifier and corresponding said new total point value in response to calculating a new point value.

2. The hydration level measurement system of claim 1 wherein said vessel identifier is an RFID tag.

3. The hydration level measurement system of claim 1 wherein said difference between said first weight reading and said second weight reading is measured in units selected from the group consisting of ounces, cups, milligrams, and grams.

4. The hydration level measurement system of claim 1 wherein said display in electronic communication with said computer displays a message indicating said computer is determining said user identifier associated with said vessel identifier.

5. The hydration level measurement system of claim 1 wherein said display in electronic communication with said computer displays a message indicating said computer is waiting for said measuring device to calculate said second weight reading.

6. The hydration level measurement system of claim 1 wherein said display in electronic communication with said computer displays a message instructing a user to remove said liquid containing vessel from said measuring device.

7. A hydration level measurement method comprising:
   (a) receiving, at a computer from a measuring device, a vessel identifier identifying a liquid containing vessel, and a first weight reading corresponding to the weight of the liquid containing vessel;
   (b) receiving at said computer from said measuring device a second weight reading corresponding to the liquid containing vessel;
   (c) calculating at said computer a point value based on a difference between said second weight reading and said first weight reading;
   (d) locating a user identifier associated with said vessel identifier;
   (e) combining at said computer said calculated point value with a previously stored total point value associated with said user identifier to calculate a new total point value;

(f) storing at said computer said new total point value;
(f) locating a user identifier associated with said vessel identifier;
(g) displaying on a display said user identifier and said new total point value;
(h) locating a challenge identifier associated with said user identifier, wherein said challenge identifier identifies a group of user identifiers assigned to a challenge and wherein said challenge has a start date, and an end date;
(i) locating the plurality of user identifiers assigned to said challenge identifier;
(j) displaying on the display the plurality of user identifiers and the stored;
(k) after the end date, determining by said computer a winner, wherein the winner is the user identifier assigned to said challenge identifier with a highest total point value within the start and end dates;
(l) displaying on the display said winner and said highest total point value.

8. The hydration level measurement method of claim 7 wherein said measuring device is a scale.

9. The hydration level measurement method of claim 7 wherein said vessel identifier is an RFID tag.

10. The hydration level measurement method of claim 7 wherein said first weight reading and said second weight reading are in units selected from the group consisting of ounces, cups, milligrams, and grams.

11. The hydration level measurement method of claim 7 wherein said display in electronic communication with said computer displays a message indicating said computer is determining said user identifier associated with said vessel identifier.

12. The hydration level measurement method of claim 7 wherein said display in electronic communication with said computer displays a message indicating said computer is waiting for said measuring device to calculate said second weight reading.

13. The hydration level measurement method of claim 7 wherein said display in electronic communication with said computer displays a message instructing a user to remove said liquid containing vessel from said measuring device.

14. A hydration level measurement system comprising:
(a) a liquid containing vessel comprising a vessel identifier;
(b) a measuring device comprising a vessel identifier detecting device and a scale;
(c) a computer connected to said measuring device and having a display, said computer configured to:
  (1) receive a start date and an end date associated with at least one challenge;
  (2) receive a plurality of user identifiers associated with said challenge;
  (3) beginning on said start date, record total point values for each of the plurality of user identifiers by:
    (i) receiving from said measuring device the vessel identifier and a first weight reading associated with the liquid containing vessel;
    (ii) receiving from said measuring device a second weight reading associated with the liquid containing vessel;
    (iii) locating a user identifier associated with said vessel identifier;
    (iv) calculating a point value based on a difference between the first weight reading and the second weight reading;
    (v) updating the stored total point value by adding said point value to the stored total point value associated with said user identifier;
    (vi) repeating steps (i)-(v) until said end date;
  (4) determine a winner associated with said challenge, wherein said winner is the user identifier assigned to said challenge with the highest total point value after said end date; and
  (5) display on the display said winner.

15. The hydration level measurement system of claim 14 wherein said user identifiers associated with said at least one challenge is displayed in a sorted order of user total point values.

16. The hydration level measurement system of claim 14 wherein said vessel identifier is an RFID tag.

17. The hydration level measurement system of claim 14 wherein said difference between said first weight reading and said second weight reading is measured in units selected from the group consisting of ounces, cups, milligrams, and grams.

* * * * *